United States Patent [19] [11] 4,173,591
Koppes et al. [45] Nov. 6, 1979

[54] PROCESS FOR THE PREPARATION OF 1,3,5-TRIFLUORO-2,4,6-TRINITROBENZENE

[75] Inventors: William M. Koppes, Adelphi; Horst G. Adolph, Silver Spring; Michael E. Sitzmann, Adelphi, all of Md.

[73] Assignee: The United States of America as represented by the Secretary of the Navy, Washington, D.C.

[21] Appl. No.: 937,281

[22] Filed: Aug. 28, 1978

[51] Int. Cl.$^2$ ............................................. C07C 79/12
[52] U.S. Cl. .................................................. 260/646
[58] Field of Search ........................................ 260/646

[56] References Cited

U.S. PATENT DOCUMENTS 4,032,377   6/1977   Benziger ............................ 260/646 X

OTHER PUBLICATIONS

Siele, Victor I. and Matsuguma, Harold J.; "Investigation of Synthetic Methods for Preparing the Fluoro Derivatives of Symmetrical Trinitrobenzene," Technical Report 2682, (Picatinny Arsenal, Dover, N.J., 1960).
Shaw, G. C., III, and Seaton, D. C.; "The Synthesis of Some Fluorine-Containing Trinitrobenzenes," J. Org. Chem., 26, 5227 (1961).
"Research on Fluorochemicals," ASD Technical Documentary Report No. ASD-TDR-62-111, Jul. 1962; Project No. 2858, Denver Research Institute.
Kaplan, Lloyd A., and Taylor, Francis, Jr., "Process Development Study of 1,3,5-Triamino-2,4,6-Trinitrobenzene," NAVORD Report 6017, Mar. 10, 1958.
O'Keefe, David M. and Gurule, Frank M.; "The Synthesis of Symmetrical Trichlorotrinitrobenzene Part 2 — Nitration with Nitric Acid; Synthesis of By-Products," SAND78-1001 Report, p. 30, Sandia Laboratories, Albuquerque, New Mexico 87185 and Livermore, California 94550, Printed Jun., 1978.

*Primary Examiner*—Leland A. Sebastian
*Attorney, Agent, or Firm*—R. S. Sciascia; A. L. Branning; R. D. Johnson

[57] ABSTRACT

A process for producing 1,3,5-trifluoro-2,4,6-trinitrobenzene by:
(1) forming a mixture of fuming sulfuric acid and potassium nitrate wherein the fuming sulfuric acid is composed of at least 25 percent by weight sulfur trioxide, and wherein the molar ratio of fuming sulfuric acid to potassium nitrate is from about 2:1 to about 3:1;
(2) adding 1,3,5-trifluorobenzene to the mixture until the molar ratio of potassium nitrate to 1,3,5-trifluorobenzene is from 6:1 to 10:1, the temperature of the mixture being maintained in the range of from about 30° C. to about 50° C. during the addition;
(3) then raising the temperature of the mixture into the range of from about 140° C. to about 160° C. where it is maintained until the optimum yield of 1,3,5-trifluoro-2,4,6-trinitrobenzene has been obtained; and
(4) isolating the product, 1,3,5-trifluoro-2,4,6-trinitrobenzene from the reaction mixture.

3 Claims, No Drawings

PROCESS FOR THE PREPARATION OF 1,3,5-TRIFLUORO-2,4,6-TRINITROBENZENE

BACKGROUND OF THE INVENTION

This invention relates to nitroaromatic compounds and more particularly to halogen substituted nitroaromatic compounds.

Lloyd A. Kaplan and Francis Taylor, Jr., in NAVORD report 6017, entitled "High Temperature Stable Explosives I," disclose a method of preparing 1,3,5-trichloro-2,4,6-trinitrobenzene from 1,3,5-trichlorobenzene using 30% fuming sulfuric acid (by weight, 30% $SO_3$, 70% $H_2SO_4$) and potassium nitrate. Good yields were obtained using molar ratios of potassium nitrate to 1,3,5-trichlorobenzene of both 4:1 and 8:1, with 8:1 being the optimal ratio. The 1,3,5-trichlorobenzene was added to the mixture of potassium nitrate and fuming sulfuric acid at a temperature of 110° C.

Denver Research Institute Report ASD-TDR-62-111, July 1962, discloses a method of producing 1,3,5-trifluoro-2,4,6-trinitrobenzene by heating 1,3,5-trifluorobenzene with a mixture of potassium nitrate and fuming sulfuric acid of unspecified strength. The molar ratio of potassium nitrate to 1,3,5-trifluorobenzene was 4:1. No mention about controlling the temperature during the addition of the 1,3,5-trifluorobenzene to the mixture of potassium nitrate and fuming sulfuric acid was made in the report. The yield of 1,3,5-trifluoro-2,4,6-trinitrobenzene was only 5.4 percent.

SUMMARY OF THE INVENTION

Accordingly, it is an object of this invention to provide an improved method of producing 1,3,5-trifluoro-2,4,6-trinitrobenzene.

Another object of this invention is to provide a method of obtaining greater yields of 1,3,5-trifluoro-2,4,6-trinitrobenzene.

These and other objectives of this invention are accomplished by providing a process for producing 1,3,5-trifluoro-2,4,6-trinitrobenzene comprising the following steps:

(1) forming a mixture of fuming sulfuric acid and potassium nitrate wherein the fuming sulfuric acid is composed of at least 25 percent by weight of sulfur trioxide, and wherein the molar ratio of fuming sulfuric acid to potassium nitrate is from about 2:1 to about 3:1;

(2) adding 1,3,5-trifluorobenzene to the mixture until the molar ratio of potassium nitrate to 1,3,5-trifluorobenzene is from 6:1 to 10:1, the temperature of the mixture being maintained in the range of from about 30° C. to about 50° C. during the addition;

(3) then raising the temperature of the mixture into the range of from about 140° C. to about 160° C. where it is maintained until the optimum yield of 1,3,5-trifluoro-2,4,6-trinitrobenzene is obtained; and (4) isolating the product 1,3,5-trifluoro-2,4,6-trinitrobenzene from the reaction mixture.

DETAILED DESCRIPTION OF THE PREFERRED EMBODIMENT

The present invention involves an improved process for producing 1,3,5-trifluoro-2,4,6-trinitrobenzene by heating 1,3,5-trifluorobenzene with a mixture of potassium nitrate and fuming sulfuric acid. The general reaction can be represented as follows:

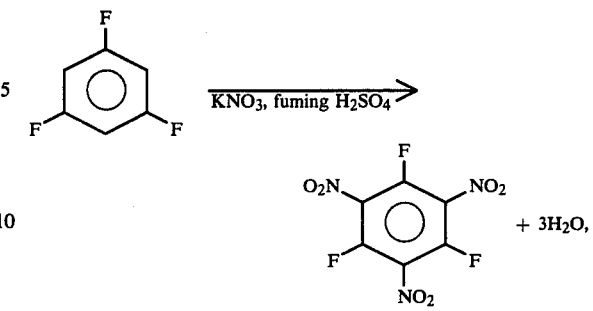

As is well known, the potassium nitrate and sulfuric acid form nitronium ions, $NO_2^+$. The nitronium ions attack the aromatic nucleus through electrophilic aromatic substitution.

It has now been discovered that by using a substantial excess of potassium nitrate over the 1,3,5-trifluorobenzene, the yield of 1,3,5-trifluoro-2,4,6-trinitrobenzene is increased. Thus, although only three moles of potassium nitrate are consumed in the reaction for each mole of 1,3,5-trifluorobenzene, the molar ratio of potassium nitrate to 1,3,5-trifluorobenzene used should be from 6:1 to 10:1 and preferably from 6.5:1 to 8:1. The excess of potassium nitrate which can be used, is limited by the increase in viscosity of the reaction mixture with increasing potassium nitrate concentration.

The use of fuming sulfuric acid in aromatic nitration reactions is well known in the art. A molar ratio of fuming sulfuric acid to potassium nitrate of from about 2:1 to about 3:1 works well. The fuming sulfuric acid must be composed of at least 25 percent by weight of sulfur trioxide (i.e., 25% oleum or 25% fuming sulfuric acid).

The temperature must be carefully controlled during this process. During the addition of 1,3,5-trifluorobenzene, the potassium nitrate-fuming sulfuric acid mixture must be kept at a temperature in the range of from about 30° C. to about 50° C. The temperature is controlled by regulating the rate at which 1,3,5-trifluorobenzene is added to the potassium nitrate-fuming sulfuric acid mixture and also through external cooling of the reaction mixture. After the initial exothermic reaction is over, the reaction mixture is heated into the range of from about 140° C. to about 160° C. but preferably from 150° C. to 156° C. where it is maintained until the optimum or desired yield of 1,3,5-trifluoro-2,4,6-trinitrobenzene is obtained. If the reaction temperature is too high, the yield will be reduced through the decomposition of the product. On the other hand, if the reaction temperature is too low, 1,3,5-trifluoro-2,4-dinitrobenzene will be produced at the expense of the 1,3,5-trifluoro-2,4,6-trinitrobenzene.

The time required for the process will vary with reaction temperature and molar ratios of the ingredients. However, the progress of the reaction may be followed through the use of gas-liquid chromotography.

Extraction with methylene chloride is the preferred method of separating the product 1,3,5-trifluoro-2,4,6-trinitrobenzene from the reaction mixture. The yields were better using this method of separation than other techniques. If necessary, concentrated sulfuric acid may be added to reduce the viscosity of the reaction mixture in order to facilitate the extraction process.

The general nature of the invention having been set forth, the following example is presented as a specific illustration thereof. It will be understood that the invention is not limited to this specific example, but is susceptible to various modifications that will be recognized by one of ordinary skill in the art.

EXAMPLE

A 3 liter 3-necked Morton flask equipped with a Teflon ® paddle stirrer and thermometer and containing 1200 ml of 30% fuming sulfuric acid (8.78 mol $SO_3$) was cooled with an ice-bath while 280 g (2.76 mol) of $KNO_3$ were added in portions to maintain a temperature not exceeding 50°. The reaction flask was placed in an oil bath and 1,3,5-trifluorobenzene (56.0 g, 0.424 mol) was added through an addition funnel. The addition rate was controlled to maintain the temperature at ca. 50°. The funnel was exchanged for a condenser protected with a drying tube (Drierite) and the mixture was heated at 153°–156° for 72 hours. The mixture was allowed to cool to 30° and extracted in the reaction flask with $CH_2Cl_2$ (3 × 1200 ml). The combined extracts were concentrated by distillation to 250 ml and this solution treated with $Na_2SO_4$ and filtered. Dry hexane (150 ml) was added to the hot filtrate. After treatment with charcoal the hot solution was filtered. A total of 60.8 g of 1,3,5-trifluoro-2,4,6-trinitrobenzene mp 80°–82° (54%) was obtained by concentration of the solution and further addition of hexane. Evaporation of the mother liquor left at 1.4 g residue composed of a 26/74 mixture of 1,3,5-trifluoro-2,4,6-trinitrobenzene and 1,3,5-trifluoro-2,4-dinitrobenzene as determined by gas-liquid phase chromotography.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A process for producing 1,3,5-trifluoro-2,4,6-trinitrobenzene comprising the following steps:
    (1) forming a mixture of fuming sulfuric acid and potassium nitrate wherein the fuming sulfuric acid is composed of at least 25 percent by weight sulfur trioxide, and wherein the molar ratio of fuming sulfuric acid to potassium nitrate is from about 2:1 to about 3:1;
    (2) adding 1,3,5-trifluorobenzene to the mixture until the molar ratio of potassium nitrate to 1,3,5-trifluorobenzene is from 6:1 to 10:1, the temperature of the mixture being maintained in the range of from about 30° C. to about 50° C. during this addition;
    (3) then raising the temperature of the mixture into the range of from about 140° C. to about 160° C. where it is maintained until the optimum yield of 1,3,5-trifluoro-2,4,6-trinitrobenzene is obtained; and finally
    (4) isolating the product 1,3,5-trifluoro-2,4,6-trinitrobenzene from the reaction mixture.

2. The process of claim 1 wherein the molar ratio of potassium nitrate to 1,3,5-trifluorobenzene is from 6.5:1 to 8:1.

3. The process of claim 1 wherein the product 1,3,5-trifluoro-2,4,6-trinitrobenzene is isolated from the reaction mixture by extraction with methylene chloride.

* * * * *